US012599473B2

(12) United States Patent
Dreyfuss et al.

(10) Patent No.: US 12,599,473 B2
(45) Date of Patent: Apr. 14, 2026

(54) TENSIONABLE KNOTLESS TISSUE REPAIR SYSTEMS AND SURGICAL METHODS

(71) Applicant: ARTHREX, INC., Naples, FL (US)

(72) Inventors: Peter J. Dreyfuss, Naples, FL (US); Kyle Anderson, Detroit, MI (US); Neal S. ElAttrache, Beverly Hills, CA (US)

(73) Assignee: ARTHREX, INC., Naples, FL (US)

( * ) Notice: Subject to any disclaimer, the term of this patent is extended or adjusted under 35 U.S.C. 154(b) by 177 days.

(21) Appl. No.: 18/507,249

(22) Filed: Nov. 13, 2023

(65) Prior Publication Data

US 2025/0152328 A1 May 15, 2025

(51) Int. Cl.
 *A61B 17/04* (2006.01)
 *A61B 17/064* (2006.01)
 *A61F 2/08* (2006.01)

(52) U.S. Cl.
 CPC ........ *A61F 2/0811* (2013.01); *A61B 17/0401* (2013.01); *A61B 17/0642* (2013.01); *A61B 2017/0414* (2013.01); *A61F 2002/0852* (2013.01); *A61F 2002/0888* (2013.01); *A61F 2220/0075* (2013.01); *A61F 2250/0012* (2013.01)

(58) Field of Classification Search
 CPC ..... A61B 2017/0414; A61F 2220/0075; A61F 2002/0852; A61F 2002/0888
 See application file for complete search history.

(56) References Cited

U.S. PATENT DOCUMENTS

| | | | |
|---|---|---|---|
| 6,767,037 | B2 | 7/2004 | Wenstrom, Jr. |
| 7,585,311 | B2 | 9/2009 | Green et al. |
| 8,100,942 | B1 | 1/2012 | Green et al. |
| 8,109,969 | B1 | 2/2012 | Green et al. |
| 8,267,964 | B2 | 9/2012 | Green et al. |
| 9,060,764 | B2 | 6/2015 | Sengun |
| 9,144,425 | B2 | 9/2015 | Kaplan |
| 9,492,158 | B2 * | 11/2016 | Stone ................... A61F 2/0811 |
| 9,615,821 | B2 * | 4/2017 | Sullivan ............. A61B 17/0401 |
| 9,737,293 | B2 | 8/2017 | Sengun et al. |
| 10,123,792 | B2 | 11/2018 | Pilgeram |
| 10,729,423 | B2 | 8/2020 | Kaiser et al. |
| 10,743,856 | B2 | 8/2020 | Durando |
| 10,835,231 | B2 | 11/2020 | Hernandez et al. |
| 10,912,549 | B2 | 2/2021 | Sengun et al. |
| 11,039,827 | B2 | 6/2021 | Sengun et al. |
| 11,357,497 | B1 * | 6/2022 | Anakwenze ....... A61B 17/0642 |
| 2007/0219558 | A1 | 9/2007 | Deutsch |
| 2011/0208240 | A1 * | 8/2011 | Stone ............... A61B 17/06166 606/232 |
| 2012/0046693 | A1 * | 2/2012 | Denham .......... A61B 17/06166 606/232 |

(Continued)

*Primary Examiner* — Alexander J Orkin

(74) *Attorney, Agent, or Firm* — Carlson, Gaskey & Olds, P.C.

(57) ABSTRACT

Tensionable knotless tissue repair systems and methods are provided for reducing and fixating tissue to bone. The proposed systems and methods may utilize one or more soft suture staple assemblies and one or more knotless suture anchors for reducing and fixating tissue to bone. The soft suture staple assemblies and knotless suture anchors may be used as part of a multi-row fixation technique for providing a desired area of footprint compression over top of the tissue.

19 Claims, 7 Drawing Sheets

(56)         References Cited

U.S. PATENT DOCUMENTS

2012/0109156 A1 *   5/2012  Overes ............... A61B 17/0483
                                            606/139
2012/0130422 A1 *   5/2012  Hootstein .......... A61B 17/0401
                                            606/228
2012/0296375 A1 *  11/2012  Thal ................... A61B 17/0401
                                            606/232
2013/0296893 A1 *  11/2013  Dean ................ A61B 17/06166
                                            606/228
2017/0071590 A1     3/2017  Macleod
2017/0273680 A1 *   9/2017  Sengun ................. A61L 31/044
2020/0178952 A1     6/2020  Sengun
2020/0253715 A1 *   8/2020  Trenhaile .............. A61F 2/0811
2021/0100547 A1 *   4/2021  Schmieding ....... A61B 17/0401
2021/0275290 A1 *   9/2021  Domecus ............. A61F 2/0811
2021/0386418 A1 *  12/2021  Dooney, Jr. .......... A61F 2/0811
2022/0008061 A1     1/2022  Durando
2024/0000445 A1 *   1/2024  Gabriel ............. A61B 17/0401
2024/0180545 A1 *   6/2024  Hart ................... A61B 17/0401

* cited by examiner

TENSIONABLE KNOTLESS TISSUE REPAIR SYSTEMS AND SURGICAL METHODS

BACKGROUND

This disclosure relates to the field of surgery, and more particularly to systems and associated surgical methods for reducing, fixating, and compressing tissue relative to bone.

Repetitive trauma to a joint, such as a knee, ankle, hip, or shoulder joint, for example, may result in the development of tissue defects (e.g., soft tissue tears, cartilage defects, etc.). If not treated, tissue defects could further deteriorate, thereby causing joint instability and discomfort.

SUMMARY

This disclosure relates to tensionable knotless tissue repair systems and methods for reducing and fixating tissue to bone. The proposed systems and methods utilize one or more soft suture staple assemblies and one or more knotless suture anchors for reducing and fixating tissue to bone. The various components of the system may be positioned as part of a multi-row fixation technique for providing a desired area of footprint compression over top of the tissue.

An exemplary surgical method may include, inter alia, inserting a soft suture staple assembly through a tissue and into a bone that underlies the tissue, inserting a knotless suture anchor into the bone at a position that is lateral to the soft suture staple assembly, connecting a suture of the knotless suture anchor to a portion of the soft suture staple assembly that extends over top of the tissue, and securing the suture back to the knotless suture anchor.

Another exemplary surgical method may include, inter alia, inserting a soft suture staple assembly through a tissue and into a bone such that a mattress stitch is arranged over top of the tissue, connecting a suture of a knotless suture anchor to the mattress stitch, tensioning the suture to compress the mattress stitch against the tissue, and fixating the suture relative to the bone with the knotless suture anchor.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
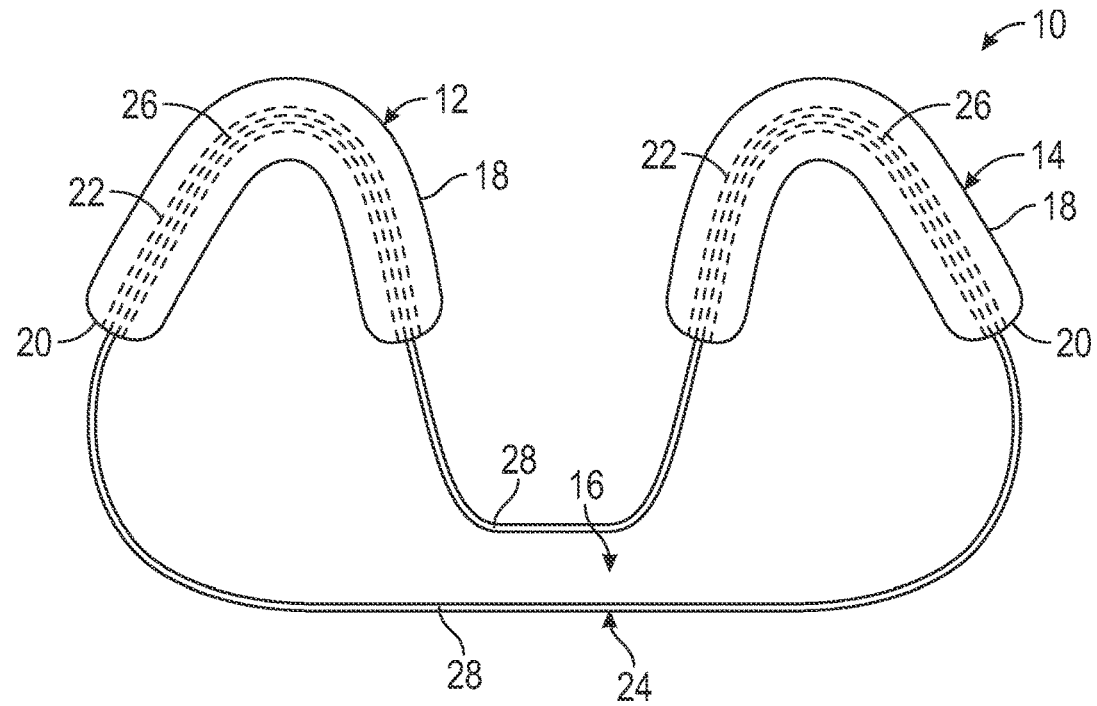
FIG. 1 illustrates a soft suture staple assembly that can be utilized as part of a surgical method for reattaching torn tissue to bone.

This disclosure is directed to tensionable knotless tissue repair systems and surgical methods for repairing tissue defects within a joint. The systems and methods described herein may be utilized to reduce, fixate, and compress tissue to bone. These and other features of this disclosure are described in further detail below.

An exemplary surgical method may include, inter alia, inserting a soft suture staple assembly through a tissue and into a bone that underlies the tissue, inserting a knotless suture anchor into the bone at a position that is lateral to the soft suture staple assembly, connecting a suture of the knotless suture anchor to a portion of the soft suture staple assembly that extends over top of the tissue, and securing the suture back to the knotless suture anchor.

In any further embodiment, the portion of the soft suture staple assembly includes a mattress stitch that extends over top of the tissue.

In any further embodiment, the mattress stitch is part of a suture that extends through and connects between a first suture sheath and a second suture sheath of the soft suture staple assembly.

In any further embodiment, the portion of the soft suture staple assembly includes a first mattress stitch and a second mattress stitch that extend over top of the tissue.

In any further embodiment, securing the suture back to the knotless suture anchor includes splicing the suture through itself to establish a suture loop that is looped around the portion.

In any further embodiment, securing the suture back to the knotless suture anchor includes tensioning the suture to further reduce the portion into place and provide a desired area of footprint compression over top of the tissue.

In any further embodiment, tensioning the suture configures the portion in a bridging pattern over top of the tissue.

In any further embodiment, connecting the suture of the knotless suture anchor to the portion of the soft suture staple assembly includes looping the suture around at least one mattress stitch of the soft suture staple assembly.

In any further embodiment, connecting the suture of the knotless suture anchor to the portion of the soft suture staple assembly includes passing the suture through at least one eyelet of the portion of the soft suture staple assembly.

In any further embodiment, the soft suture staple assembly is a medial row fixation device, and the knotless suture anchor is a lateral row fixation device.

Another exemplary surgical method may include, inter alia, inserting a soft suture staple assembly through a tissue and into a bone such that a mattress stitch is arranged over top of the tissue, connecting a suture of a knotless suture anchor to the mattress stitch, tensioning the suture to compress the mattress stitch against the tissue, and fixating the suture relative to the bone with the knotless suture anchor.

In any further embodiment, fixating the suture relative to the bone with the knotless suture anchor includes inserting the knotless suture anchor into the bone at a position that is lateral to the soft suture staple assembly.

In any further embodiment, the knotless suture anchor is inserted into the bone before connecting the suture to the mattress stitch.

In any further embodiment, connecting the suture to the mattress stitch includes splicing the suture through itself to establish a suture loop that is looped around the mattress stitch.

In any further embodiment, the knotless suture anchor is inserted into the bone after connecting the suture to the mattress stitch.

In any further embodiment, fixating the suture relative to the bone with the knotless suture anchor includes feeding the suture through an eyelet of the knotless suture anchor, positioning the eyelet within a socket formed in the bone, tensioning the suture, and moving an anchor body of the knotless suture anchor toward the eyelet within the socket, thereby trapping the suture between the bone and the anchor body.

In any further embodiment, tensioning the suture configures the mattress stitch in a bridging pattern over top of the tissue.

In any further embodiment, the mattress stitch is V-shaped in the bridging pattern.

In any further embodiment, the mattress stitch is part of a suture that extends through and connects between a first suture sheath and a second suture sheath of the soft suture staple assembly.

FIG. 1 illustrates a soft suture staple assembly 10 that may be utilized during surgical methods for attaching tissue (e.g., ligament, tendon, graft, etc.) to bone. Although the soft suture staple assembly 10 is described herein for use during surgical methods for reapproximating and fixating torn tissue back to bone, the systems and methods of this disclosure could be utilized to repair any type of tissue effect. The soft suture staple assembly 10 of FIG. 1 could be used in conjunction with a variety of orthopedic surgical repairs, including but not limited to rotator cuff repairs, Achilles tendon repairs, patellar tendon repairs, ACL/PCL reconstructions, hip and shoulder reconstructions, among many others.

In this disclosure, the soft suture staple assembly 10 is referred to as a "soft" construct because it is made exclusively of soft, suture-based materials. The suture-based materials may include soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure.

The soft suture staple assembly 10 may include a first suture sheath 12, a second suture sheath 14, and a suture 24 that connects the first suture sheath 12 and the second suture sheath 14. When inserted into tissue and/or bone, the soft suture staple assembly 10 may function similarly to a surgical staple, with the first suture sheath 12 establishing a first prong of the staple, the second suture sheath 14 establishing a second prong of the staple, and the suture 24 establishing a bridge of the staple.

The first suture sheath 12 and the second suture sheath 14 may each include a tubular body 18 that extends between opposing ends 20. The opposing ends 20 may be open ends, and the tubular body 18 may include a bore 22 that extends between the opposing ends 20. The first suture sheath 12 and the second suture sheath 14 may be made of flexible materials, such as braided, woven, or knitted structures made of yarns, fibers, filaments, sutures or similar materials, or combinations of these materials. In an embodiment, the first and second suture sheaths 12, 14 are constructed of polyester suture materials. However, other materials may also be suitable to construct each of the first suture sheath 12 and the second suture sheath 14 within the scope of this disclosure.

The suture 24 may be routed through the bore 22 of each of the first suture sheath 12 and the second suture sheath 14. The suture 24 may be configured to provide a closed loop 16 that interconnects the first and second sheaths 12, 14. For example, the suture 24 may be spliced, swaged, knotted, etc. in order to form the closed loop 16.

The suture 24 may be FiberWire®, FiberTape®, or any other suitable suture product. FiberWire® and FiberTape® are suture products marketed and sold by Arthrex, Inc. However, other suture products could be utilized for the suture 24 within the scope of this disclosure.

First strand portions 26 of the suture 24 may be accommodated within the first suture sheath 12 and the second suture sheath 14 by routing these portions through the bores 22 and the opposing ends 20. Second strand portions 28 of the suture 24 may extend outside of the tubular bodies 18 and connect between the first suture sheath 12 and the second suture sheath 14 when the suture 24 is connected to the first and second suture sheaths 12, 14.

Tensioning the suture 24 may assist in bunching together the first suture sheath 12 and the second suture sheath 14 of the soft suture staple assembly 10 after the sheaths have been inserted into tissue and/or bone. The first and second suture sheaths 12, 14 may therefore form anchoring clusters that promote adequate fixation of the soft suture staple assembly 10 relative to the tissue and/or bone.

FIGS. 2-10 schematically illustrate various aspects associated with a surgical method for attaching a tissue 30 (e.g., ligament, tendon, graft, etc.) to a bone 32. The tissue 30 may have torn away from the bone 32 during vigorous exercise or sporting activities, for example. When such tears occur, reattachment is often necessary to repair the tissue defect. Although the surgical method is described herein for reapproximating and fixating torn tissue back to bone, the surgical systems and methods of this disclosure could be utilized to repair any type of tissue defect.

The surgical method schematically illustrated in FIGS. 2-10 could be used in conjunction with a variety of orthopedic surgical repairs, including but not limited to rotator cuff repairs, Achilles tendon repairs, patellar tendon repairs, ACL/PCL reconstructions, hip and shoulder reconstructions, among many others. The bone 32 may therefore be associated with any joint of the human musculoskeletal system (e.g., shoulder, knee, hip, ankle, etc.).

In an embodiment, the surgical method is performed as an arthroscopic procedure by working through various arthroscopic portals. However, the exemplary surgical method could alternatively be performed as an open procedure within the scope of this disclosure. As detailed below, the exemplary surgical method may be employed to reduce and then reattach the tissue 30 to the bone 32 in a manner that enhances footprint compression to maximize tissue-to-bone contact.

Figure 2:
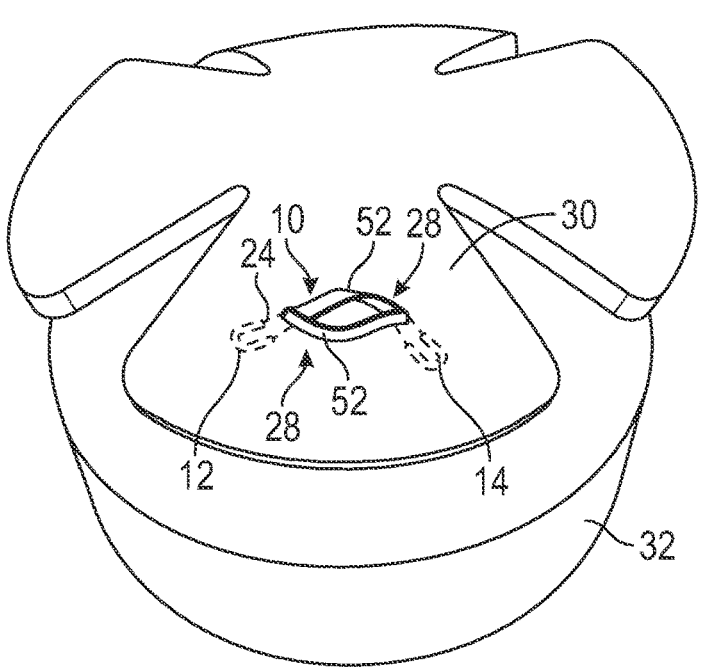
FIG. 2 schematically illustrates a step of a surgical method for reattaching torn tissue to bone.

Referring first to FIG. 2, the surgical method may begin by implanting the soft suture staple assembly 10. If necessary, the bone 32 may be appropriately prepared (e.g., by debriding, creating a bleeding bone bed, preparing bone sockets, etc.) and the tissue 30 may be approximated to a desired position relative to the bone 32 prior to implanting the soft suture staple assembly 10. The first suture sheath 12 and the second suture sheath 14 of the soft suture staple assembly 10 may be inserted through the tissue 30 and then into the underlying bone 32 to implant the soft suture staple assembly 10 therein. The first suture sheath 12 and the second suture sheath 14 of the soft suture staple assembly 10 may be inserted through the tissue 30 and into the bone 32 either simultaneously or sequentially.

Once inserted, the first suture sheath 12 and the second suture sheath 14 may establish a medial row of fixation devices within the bone 32. In an embodiment, the first suture sheath 12 and the second suture sheath 14 of the medial row are placed at or near the articular margin of the bone 32. However, other implantation locations could be selected based on the performing surgeon's preferences. Notably, although only one soft suture staple assembly 10 is illustrated as being part of the medial row in the illustrated embodiment, a greater or fewer number of fixation devices could be utilized as part of the surgical method within the scope of this disclosure. For example, the medial row could include multiple soft suture staple assemblies 10 in some implementations of the surgical method.

Portions of the suture 24 may extend over top of the tissue 30 after implanting the soft suture staple assembly 10. For example, the second strand portions 28 may establish mattress stitches 52 that extend over top of the tissue 30. The mattress stitches 52 may at least partially reduce the tissue 30 down against the bone 32.

Figures 3, 4, 5:
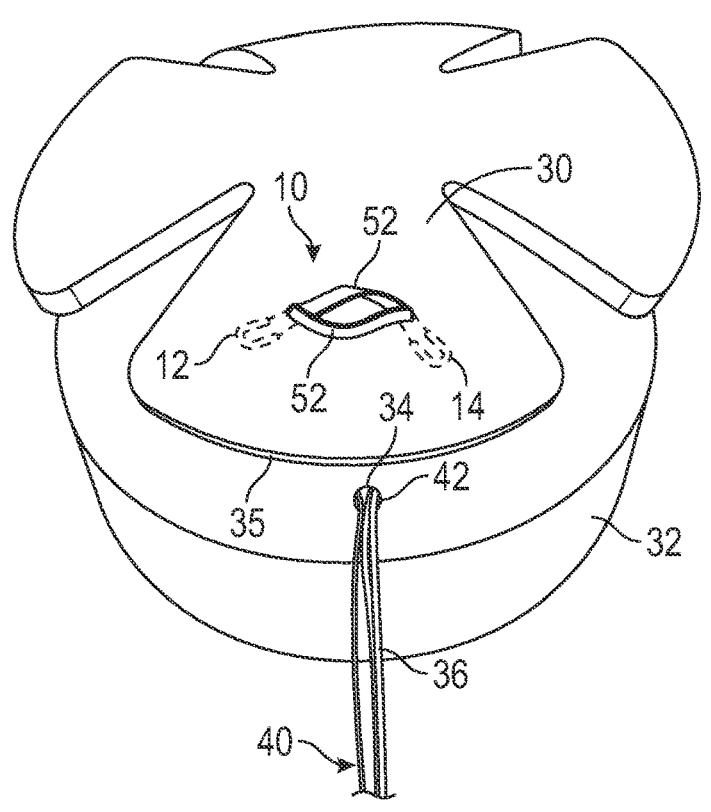
FIG. 3 illustrates another step of a surgical method for reattaching torn tissue to bone.
FIGS. 4 and 5 illustrate an exemplary knotless suture anchor.

Referring next to FIG. 3, the surgical method can proceed by implanting a lateral row of fixation devices into the bone 32. The lateral row of fixation devices may include one or more knotless suture anchors 34. The knotless suture anchors 34 do not require the need to tie any knots in the various structures for achieving fixation. As further discussed below, the knotless suture anchors 34 provide the ability to tension aspects of the medial row of fixation devices where tension would not otherwise be possible.

In an embodiment, the knotless suture anchor(s) 34 of the lateral row is placed laterally from an edge 35 of the tissue 30 and slightly distal to the greater tuberosity of the bone 32. The knotless suture anchor 34 is therefore placed laterally from the soft suture staple assembly 10. However, other implantation locations could be selected based on the performing surgeon's own preferences and depending on the type of orthopedic procedure being performed. Notably, although one knotless suture anchor 34 is illustrated as being part of the lateral row in the illustrated embodiment, a greater number of knotless suture anchors could be utilized as part of the surgical method within the scope of this disclosure.

Each knotless suture anchor 34 may be pre-loaded with one or more sutures 36. The sutures 36 may include individual suture strands, multiple suture strands, suture tape, or any other suture-like product.

FIGS. 4-7 illustrate exemplary knotless suture anchors that can be utilized as the knotless suture anchors 34 of the lateral row of fixation devices when performing the surgical methods described herein. Knotless suture anchors similar to those shown in FIGS. 4-7 may be utilized either alone or in combination with one another as part of the lateral row during the surgical method.

An exemplary knotless suture anchor 34-1 is illustrated in FIGS. 4 and 5. In this embodiment, the knotless suture anchor 34-1 is a "soft" anchor assembly made exclusively of soft, suture-based materials. The suture-based materials may include soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. The soft, suture-based materials allow the knotless suture anchor 34-1 to be inserted into bone sockets/holes and bunch together, collapse, expand and/or change shape to fixate within the socket/hole.

The knotless suture anchor 34-1 may include an anchor body 38-1 and a suture 36 received through the anchor body 38-1. A shuttle device 40 may be spliced through portions of the suture 36. The shuttle device 40 may be a passing wire or another suture, for example.

The anchor body 38-1 of the knotless suture anchor 34-1 may be inserted into a socket 42 formed in the bone 32 (see FIG. 5). The socket 42 may be a preformed opening formed in the bone 32 that is configured for receiving the anchor body 38-1.

The shuttle device 40 may be pre-assembled to the suture 36 as shown in FIG. 4, and the suture 36 may form a suture loop 44 after the suture 36 is shuttled through itself as shown in FIG. 5. For example, a suture tail 46 of the suture 36 may be passed through an eyelet 48 of the shuttle device 40 (in the direction of arrow A of FIG. 4), and then a free end 50 of the shuttle device 40 may be pulled (in the direction of arrow B of FIG. 4) to allow the suture 36 to pass through itself and form the suture loop 44. The perimeter of the suture loop 44 is adjustable to allow the construct to be self-cinching and to adjust the tension on the construct that is to be fixated.

In an exemplary embodiment, the knotless suture anchor 34 of the lateral row may include the design of the knotless suture anchor 34-1 for performing the surgical method steps herein. However, other type of suture anchors or combinations of suture anchors are contemplated within the scope of this disclosure.

Figure 6:
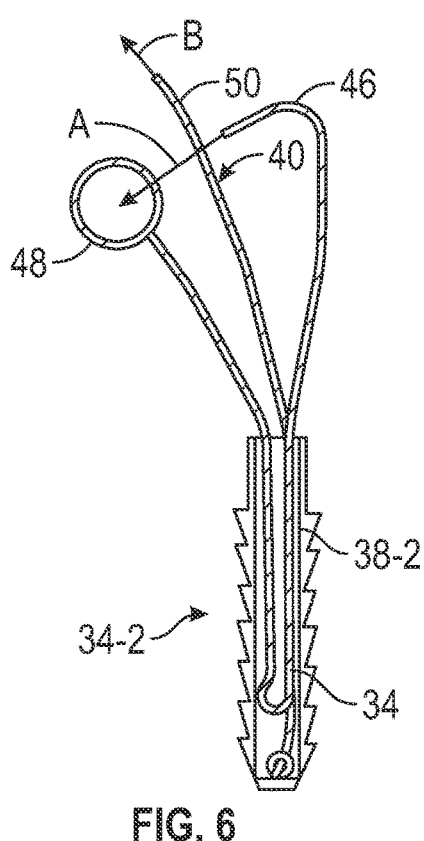
FIGS. 6 and 7 illustrate another exemplary knotless suture anchor.
Figure 7:
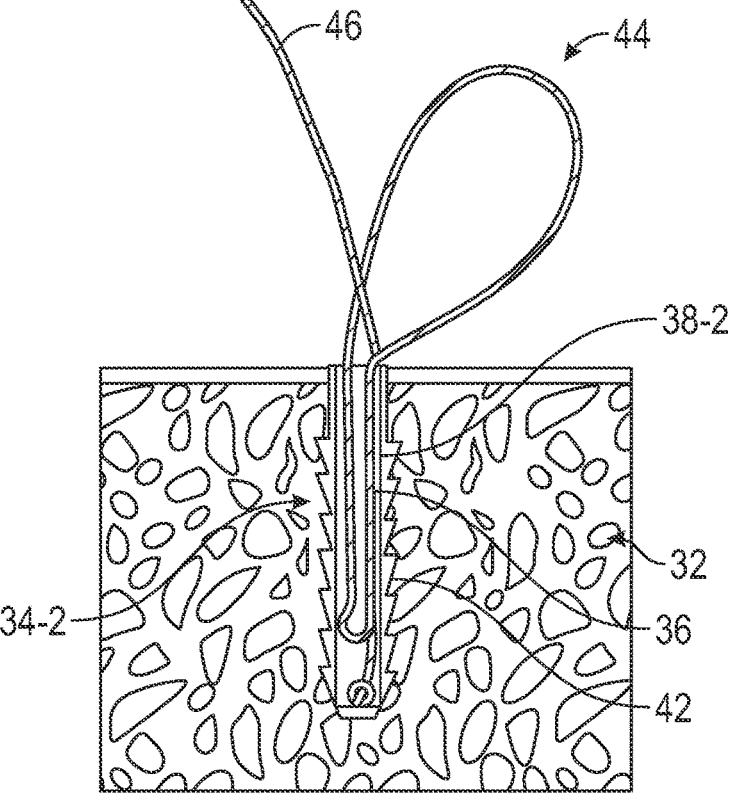

Another exemplary knotless suture anchor 34-2 is illustrated in FIGS. 6 and 7. The knotless suture anchor 34-2 may include an anchor body 38-2 and a suture 36 received through the anchor body 38-2. In this embodiment, the anchor body 38-2 is a relatively rigid plastic body, and the knotless suture anchor 34-2 is therefore not considered to be a "soft" anchor assembly.

The knotless suture anchor 34-2 may include a tensionable knotless mechanism that is similar to that of the knotless suture anchor 34-1. For example, a shuttle device 40 may be spliced through portions of the suture 36. The shuttle device 40 may be a passing wire or another suture, for example. The anchor body 38-2 of the knotless suture anchor 34-2 may be inserted into a socket 42 formed in the bone 32 (see FIG. 7). The socket 42 may be a preformed opening formed in the bone 32 that is configured for receiving the anchor body 38-2. The shuttle device 40 may be pre-assembled to the suture 36 as shown in FIG. 6 and may be utilized to form a suture loop 44 after the suture 36 is shuttled through itself as shown in FIG. 7. For example, a suture tail 46 of the suture 36 may be passed through an eyelet 48 of the shuttle device 40 (in the direction of arrow A of FIG. 6), and then a free end 50 of the shuttle device 40 may be pulled (in the direction of arrow B of FIG. 6) to allow the suture 36 to pass through itself and form the suture loop 44. The perimeter of suture loop 44 is adjustable to allow the construct to be self-cinching and to adjust the tension on the construct that is to be fixated by the knotless suture anchor 34-2.

In an exemplary embodiment, the knotless suture anchor 34 of the lateral row may include the design of the knotless suture anchor 34-2 (rather than that of the knotless suture anchor 34-1, for example) for performing the surgical method steps described herein. However, other type of suture anchors or combinations of suture anchors are contemplated within the scope of this disclosure.

Figures 8, 9:
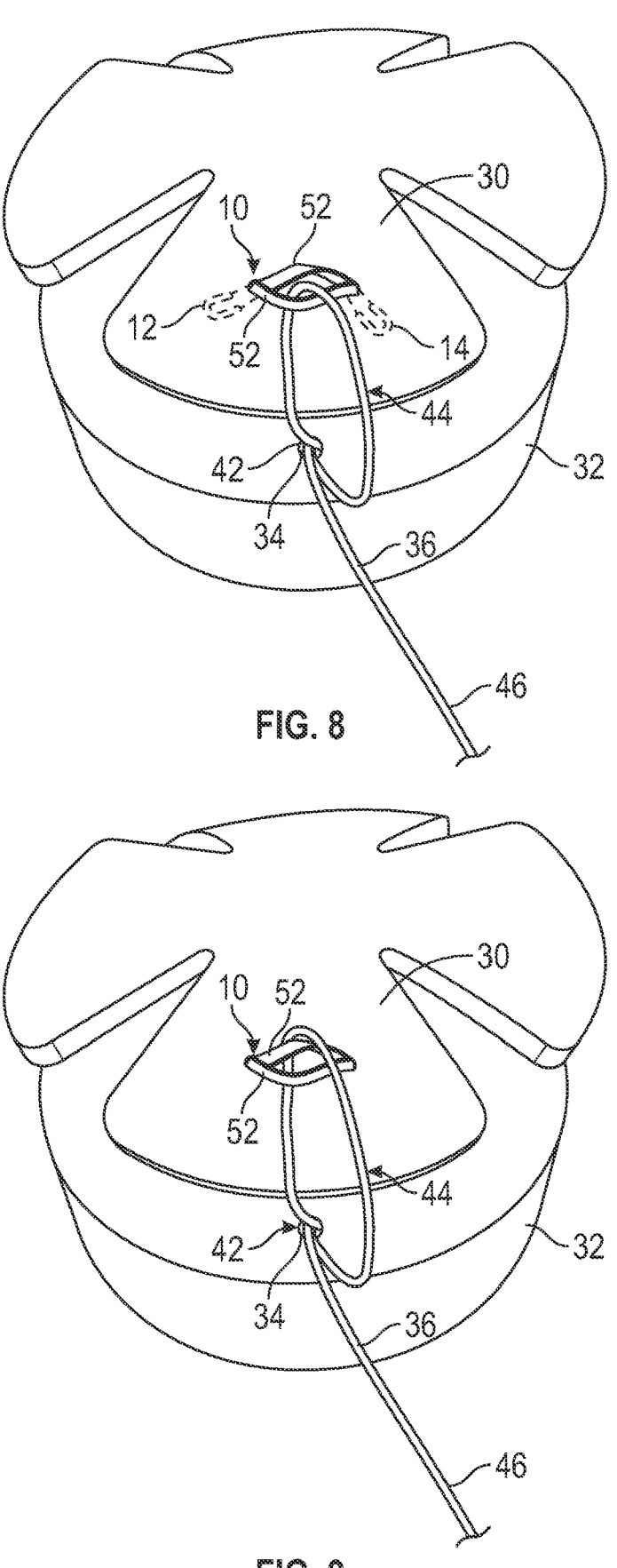
FIG. 8 illustrates another step of a surgical method for reattaching torn tissue to bone.
FIG. 9 illustrates an optional step of a surgical method for reattaching torn tissue to bone.

Referring now to FIG. 8, the suture 36 from the knotless suture anchor 34 may be connected to the soft suture staple assembly 10. This connection can be achieved by looping the suture 36 around one (see FIG. 8) or both (see FIG. 9) of the mattress stitches 52 previously established by inserting the soft suture staple assembly 10 through the tissue 30 and into the bone 32. The suture 36 may then be secured back to the knotless suture anchor 34 by splicing the suture 36 through itself using the shuttle device 40. The splicing procedure forms the suture loop 44 around the mattress stitch 52, thereby securing the suture 36 to the soft suture staple assembly 10. The suture 36 may then be further tensioned to reduce the mattress stitches 52 further down into place and more firmly fixate the tissue 30 against the bone 32. The suture tail 46 of the suture 36 may be removed (e.g., cut) once tensioning is complete.

Figure 10:
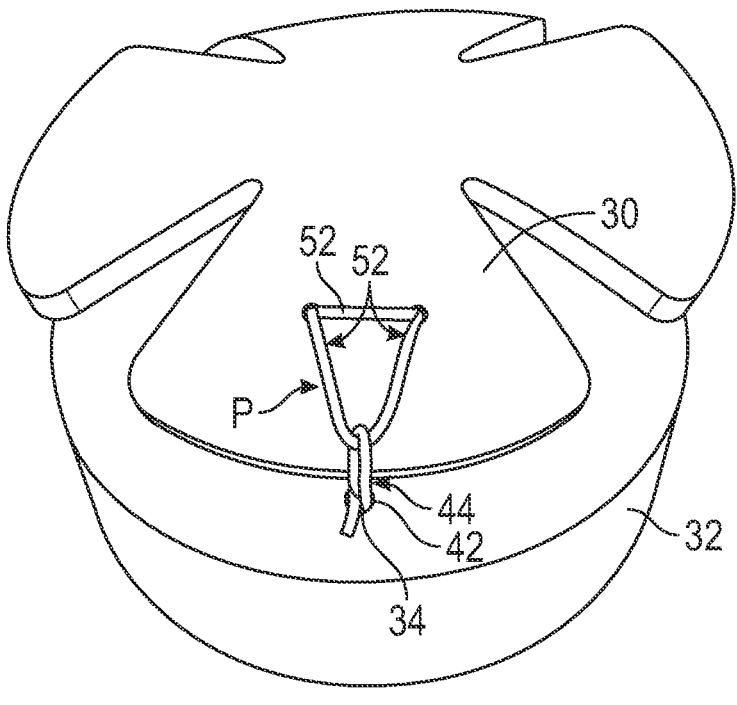
FIG. 10 illustrates a final repair construct of a surgical method for reattaching tissue to bone.
Figure 11:
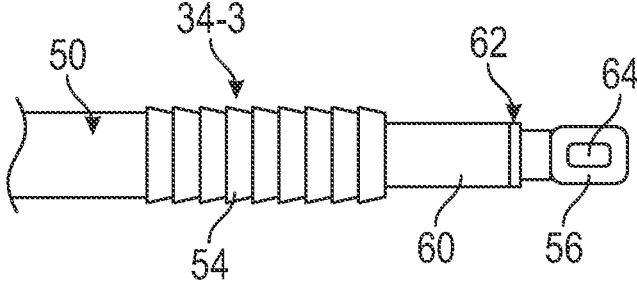
FIGS. 11 and 12 illustrate yet another exemplary knotless suture anchor.

The final construct achieved by the surgical method is shown in FIG. 10. The mattress stitch 52 of the soft suture staple assembly 10 may establish a bridging pattern P that provides a desired area of footprint compression over top of the tissue 30 once a desired amount of tension has been achieved. As part of the bridging pattern P, the mattress stitch 52 may be arranged in a V-shape that extends between the locations where the soft suture staple assembly 10 extends through the tissue 30 and the location where the suture loop 44 connects to the mattress stitch 52. However, other bridging configurations using any number of soft suture staple assemblies 10 and knotless suture anchors 34 could be achieved as part of the surgical method In the above embodiments, the suture 36 is connected to the suture 24 of the soft suture staple assembly 10 after implanting the lateral row knotless suture anchor 34 into the bone 32. However, other implementations are possible. For example, the knotless suture anchor 34 could be implanted into the bone 32 after making the connection with the suture 24 (e.g., by looping the suture 36 around the one or more mattress stitches 52) by employing the design of another exemplary knotless suture anchor 34-3 shown in FIGS. 11-12.

The knotless suture anchor 34-3 may include an anchor body 54 and an eyelet 56. In this embodiment, the anchor body 54 and the eyelet 56 are relatively rigid plastic structures and thus the knotless suture anchor 34-3 is not considered to be a "soft" anchor assembly.

The anchor body 54 may be pre-loaded onto a driver 58. The anchor body 54 may be configured as a screw or an interference plug that is appropriately cannulated for receiving a shaft 60 of the driver 58. The eyelet 56 may be provided at a distal end 62 of the driver 58. The eyelet 56 may be releasably attached to the distal end 62 and may include an aperture 64 for receiving one or more sutures.

Figure 12:
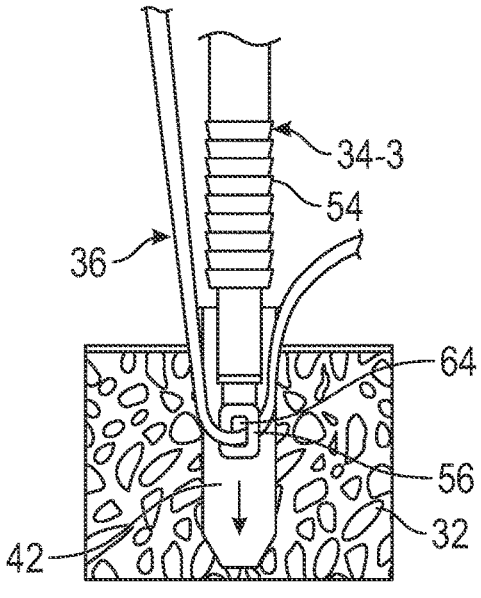

The anchor body 54 and the eyelet 56 of the knotless suture anchor 34-3 may be inserted into a socket 42 formed in the bone 32 (see FIG. 12). The socket 42 may be a preformed opening formed in the bone 32 that is configured for receiving the anchor body 54 and the eyelet 56. The suture 36 may be loaded through the eyelet 56, and then the eyelet 56 may be inserted into the socket 42. The suture 36 may then be tensioned prior to moving the anchor body 54 down toward the eyelet 56 within the socket 42. Once implanted within the socket 42, the anchor body 54 may trap the suture 36 between the bone 32 and the anchor body 54 in order to fixate the suture 36 in place. The knotless suture anchor 34-3 therefore provides the ability to implant the lateral row knotless suture anchor 34 after connecting the suture 36 to the medial row soft suture staple assembly 10 during the surgical method.

Figure 13:
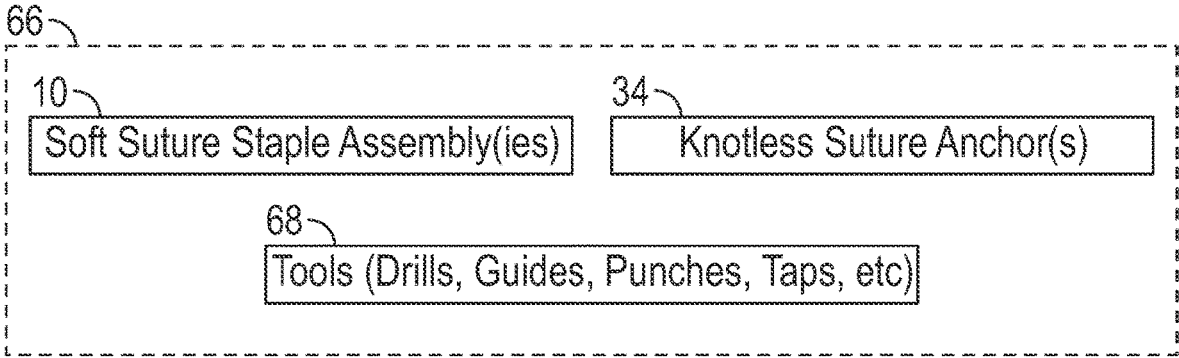
FIG. 13 schematically illustrates an exemplary tensionable knotless tissue repair system.

FIG. 13 schematically illustrates an exemplary tensionable knotless tissue repair system 66 that may be provided for performing the surgical method described above. The tensionable knotless tissue repair system 66 may be provided in the form of a surgical kit that includes all the necessary tools and components for performing surgical methods for reducing and reattaching torn tissue to bone. In an embodiment, the tensionable knotless tissue repair system 66 may include at least the following components:

1. At least one soft suture staple assembly 10;
2. At least one knotless suture anchor 34; and
3. Various tools 68 (e.g., disposable drills, drill guides, punches, taps, etc.) for inserting the soft suture staple assembly 10 and the knotless suture anchor 34 into bone.

Other components or different combinations of components could be provided as part of the tensionable knotless tissue repair system 66 within the scope of this disclosure. For example, the tensionable knotless tissue repair system 66 could include various templates, scorers, curettes, and/or measuring devices that may be utilized to help prepare both the tissue 30 and the bone 32 for performing the surgical methods discussed herein.

Figures 14, 15:
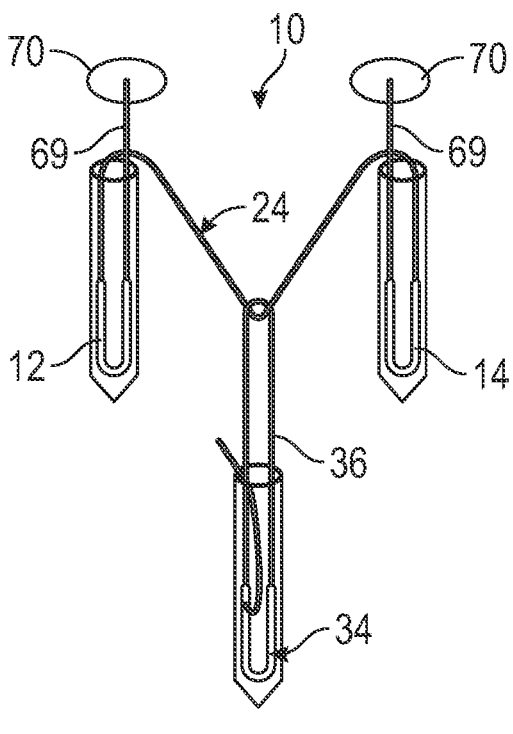
FIG. 14 schematically illustrates another exemplary soft suture staple assembly.
FIG. 15 schematically illustrates yet another exemplary soft suture staple assembly.

In the above embodiments, the suture 24 of the soft suture staple assembly 10 is configured in the form of the closed loop 16 that interconnects the first suture sheath 12 and the second suture sheath 14. However, other implantations of the soft suture staple assembly 10 are contemplated within the scope of this disclosure. For example, as shown in FIGS. 14 and 15, the suture 24 may alternatively have unconnected free end portions 69 that extend outside of the first suture sheath 12 and the second suture sheath 14. In such configurations, the suture 24 is not configured to form the closed loop. The unconnected free end portions 69 may connect, for example, to surgical buttons 70 that can be fixated over top of tissue (see, e.g., FIG. 14), or could alternatively include eyelets 72 that are configured to receive the suture 36 of the lateral row knotless suture anchor 34 for connecting the suture 36 to the soft suture staple assembly 10 (see, e.g., FIG. 15).

The tensionable knotless tissue fixation systems and surgical methods described herein may be utilized to knotlessly approximate, fixate, and compress tissue to bone. The proposed systems and methods provide multi-point knotless fixation configurations for fixating tissue to bone. The use of a soft suture staple assembly in combination with a laterally placed knotless suture anchor provides the ability to add tension to the medial side of the fixation construct for maintaining footprint compression, thereby maximizing tissue-to-bone contact.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
inserting a soft suture staple assembly through a tissue and into a bone that underlies the tissue,
wherein the soft suture staple assembly includes a first suture sheath, a second suture sheath, and a suture routed through a bore of each of the first suture sheath and the second suture sheath to form a closed loop that interconnects the first suture sheath and the second suture sheath,
wherein inserting the soft suture staple assembly includes simultaneously inserting the first suture sheath and the second suture sheath of the soft suture staple assembly through the tissue and into the bone;
inserting a knotless suture anchor into the bone at a position that is lateral to the soft suture staple assembly;
connecting a suture of the knotless suture anchor to a portion of the closed loop that extends over top of the tissue; and
securing the suture back to the knotless suture anchor.

2. The surgical method as recited in claim 1, wherein the portion of the closed loop includes a mattress stitch that extends over top of the tissue.

3. The surgical method as recited in claim 2, wherein the mattress stitch is part of the suture that is routed through the first suture sheath and the second suture sheath of the soft suture staple assembly.

4. The surgical method as recited in claim 2, wherein the portion of the closed loop includes a first mattress stitch and a second mattress stitch that extend over top of the tissue.

5. The surgical method as recited in claim 1, wherein securing the suture back to the knotless suture anchor includes:
splicing the suture through itself to establish a suture loop that is looped around the portion.

6. The surgical method as recited in claim 5, wherein securing the suture back to the knotless suture anchor includes:
tensioning the suture to further reduce the portion into place and provide a desired area of footprint compression over top of the tissue, wherein tensioning the suture configures the portion in a bridging pattern over top of the tissue.

7. The surgical method as recited in claim 1, wherein connecting the suture of the knotless suture anchor to the portion of the closed loop includes:
looping the suture around at least one mattress stitch of the closed loop.

8. The surgical method as recited in claim 1, wherein connecting the suture of the knotless suture anchor to the portion of the closed loop includes:
passing the suture through at least one eyelet of the portion of closed loop.

9. The surgical method as recited in claim 1, wherein the soft suture staple assembly is comprised exclusively of soft, suture-based materials.

10. A surgical method, comprising:
inserting a soft suture staple assembly through a tissue and into a bone, wherein the soft suture staple assembly includes a first sheath, a second suture sheath, and a suture routed through a bore of each of the first suture sheath and the second suture sheath to form a closed loop that interconnects the first suture sheath and the second suture sheath;
connecting a suture of a knotless suture anchor to a portion of the closed loop that extends over top of the tissue;
tensioning the suture to compress the portion of the closed loop against the tissue; and
fixating the suture relative to the bone with the knotless suture anchor.

11. The surgical method as recited in claim 10, wherein fixating the suture relative to the bone with the knotless suture anchor includes:
inserting the knotless suture anchor into the bone at a position that is lateral to the soft suture staple assembly.

12. The surgical method as recited in claim 11, wherein the knotless suture anchor is inserted into the bone before connecting the suture to the portion of the closed loop.

13. The surgical method as recited in claim 12, wherein connecting the suture to the portion of the closed loop includes:
splicing the suture through itself to establish a suture loop that is looped around the portion of the closed loop.

14. The surgical method as recited in claim 11, wherein the knotless suture anchor is inserted into the bone after connecting the suture to the portion of the closed loop.

15. The surgical method as recited in claim 14, wherein fixating the suture relative to the bone with the knotless suture anchor includes:
feeding the suture through an eyelet of the knotless suture anchor;
positioning the eyelet within a socket formed in the bone;
tensioning the suture; and
moving an anchor body of the knotless suture anchor toward the eyelet within the socket, thereby trapping the suture between the bone and the anchor body.

16. The surgical method as recited in claim 15, wherein tensioning the suture configures the portion of the closed loop in a bridging pattern over top of the tissue.

17. The surgical method as recited in claim 10, wherein tensioning the suture configures the portion of the closed loop in a bridging pattern over top of the tissue.

18. The surgical method as recited in claim 10, wherein the closed loop includes a mattress stitch that is part of the suture that is routed through the first suture sheath and the second suture sheath of the soft suture staple assembly.

19. A surgical method, comprising:
inserting a first suture sheath of a soft suture staple assembly through a tissue and into a bone that underlies the tissue, wherein the soft suture staple assembly includes the first suture sheath, a second suture sheath, and a first suture routed through a bore of each of the first sheath and the second sheath to form a closed loop that interconnects the first suture sheath and the second suture sheath;
after inserting the first suture sheath, inserting the second suture sheath of the soft suture staple assembly through the tissue and into the bone,
wherein, after inserting the first suture sheath and the second suture sheath through the tissue and into the bone, a portion of the closed loop extends over top of the tissue;

inserting a knotless suture anchor into the bone at a
   position that is lateral to the soft suture staple assembly;
looping a second suture of the knotless suture anchor
   around the portion of the closed loop that extends over
   top of the tissue; and
securing the second suture back to the knotless suture
   anchor.

\* \* \* \* \*